United States Patent [19]

Rosenberg et al.

[11] Patent Number: 4,873,317

[45] Date of Patent: Oct. 10, 1989

[54] METHOD OF SEPARATING OR PURIFYING PROTEINS AND OTHER BIOPOLYMERS

[76] Inventors: Melvyn Rosenberg, 12 Yeda Am Street; Ilana Eli, 22 Shazar Street, both of Ramat-Gan, Israel

[21] Appl. No.: 22,225

[22] Filed: Mar. 5, 1987

[30] Foreign Application Priority Data

Mar. 13, 1986 [IL] Israel ........................................ 78130

[51] Int. Cl.⁴ .......................... C07K 3/12; C07K 3/20; C07K 3/24; C12P 21/00
[52] U.S. Cl. .................................. 530/412; 530/412; 530/413; 530/414; 530/415; 530/416; 530/417; 530/418; 530/422; 530/423; 530/424; 530/425; 530/426; 435/68; 435/99; 435/101
[58] Field of Search ............................... 530/412–418, 530/422–426; 435/68, 101, 99

[56] References Cited

U.S. PATENT DOCUMENTS

| 4,649,110 | 3/1987 | Shilo et al. | 435/68 |
| 4,704,360 | 11/1987 | Shoham et al. | 435/99 |

Primary Examiner—Delbert R. Phillips
Assistant Examiner—Abdel A. Mohamed
Attorney, Agent, or Firm—Benjamin J. Barish

[57] ABSTRACT

A method for the separation or purification of biopolymers comprises adsorbing the biopolymer on the surface of liquid oil droplets; and separating the adsorbed biopolymer from the oil droplets. The adsorbed biopolymer is separated from the oil droplets by mixing the droplets in an aqueous liquid, removing the lower aqueous phase and adding a fresh aqueous phase to the droplets, cooling the mixture to solidify and coalesce the oil and to cause it to release the adsorbed biopolymer to the fresh liquid, separating the fresh liquid and the biopolymer from the coalesced oil, separating the biopolymer from the fresh liquid.

16 Claims, 1 Drawing Sheet

METHOD OF SEPARATING OR PURIFYING PROTEINS AND OTHER BIOPOLYMERS

BACKGROUND OF THE INVENTION

The present invention relates to a method for the separation or purification of proteins and other biopolymers. The invention is believed to be particularly applicable for the separation or purification of proteins such as interleukin-2, insulin, $\alpha$- and $\gamma$-interferon, antibodies, growth hormones, and various enzymes.

The separation or purification of proteins and other biopolymers on the basis of their relative hydrophobic properties is of considerable basic and applied interest. The main techniques currently employed are based on chromatography utilizing solid hydrophobic phases such as n-alkyl and aryl agaroses, and n-alkyl-bonded silica supports. Following adsorption of the amphipathic moieties to the solid support, elution may be carried out by decreasing salt gradients, or increasing the concentrations of detergents or organic solvents. Problems which may be encountered with such an approach include denaturation, elution and the expense of processing large quantities of material.

The present invention relates to an alternative procedure for the separation of proteins and other biopolymers.

BRIEF SUMMARY OF THE INVENTION

According to the present invention, there is provided a method for the separation of biopolymers comprising the steps of adsorbing the amphipathic biopolymer on the surface of liquid oil droplets; and separating the adsorbed biopolymer from the liquid oil droplets.

In the preferred embodiments of the invention described below, the adsorbed bipolymer is absorbed on the surface of the oil droplets by mixing the droplets in an aqueous liquid; separation is achieved by removing the lower aqueous phase and adding a fresh aqueous phase to the droplets, cooling the mixture to solidify and coalesce the oil and to cause it to release the adsorbed biopolymer to the fresh liquid, separating the fresh liquid and the biopolymer from the coalesced oil, and separating the biopolymer from the fresh liquid. The oil droplets are preferably of liquid hexadecane, but it will be appreciated that other oil droplets could be used, for example, octadecane or vegetable oils, e.g., coconut oil, preferably having melting points of $-20°$ C. to 45° C., or silicone-based oils, or fluorocarbons, or other oils.

Further features and advantages of the invention will be apparent from the description below.

BRIEF DESCRIPTION OF THE DRAWINGS

The invention is described below with respect to several examples and the accompanying tables and drawings; in the drawings.

DESCRIPTION OF PREFERRED EMBODIMENTS

EXAMPLES

Figure 1:
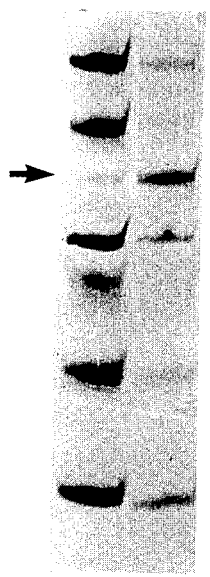
FIG. 1 illustrates the results produced in the SDS-Polyacrylamide gel electrophoresis of the seven marker proteins mixed in the presence of hexadecane.

Following are several examples of the invention:

EXAMPLE 1—Extraction of a Commercial Protein Mixture

The commercial proteins mixture used was the Dalton Mark VII-L (Sigma, St. Louis, MO), a lyophilized mixture of seven proteins, as follows:

1. bovine albumin, approx. 66 Kd;
2. ovalbumin, approx. 45 kD;
3. glyceraldehyde-3-phosphate dehydrogenase from rabbit muscle, approx. 36 kD (subunit);
4. carbonic anhydrase from bovine erythrocytes, approx. 29 kD;
5. treated trypsinogen from bovine pancreas, approx. 24 kD;
6. trypsin inhibitor from soybean, approx. 20.1 kD;
7. $\alpha$-lactalbumin, approx. 14.2 kD.

The mixture was dissolved in distilled water to a final concentration of 1 mg/ml protein. To one ml of aqueous protein suspension in an acid-washed, round bottom test tube, 0.5 ml hexadecane was added, and the mixture vortexed for 2 min at room temperature. Following phase separation, the lower aqueous phase was removed; one ml of distilled water was added to the test tube, and the contents incubated at 4 C.

Following freezing of the hexadecane layer, the test tube was allowed to equilibrate with room temperature and the lower aqueous phase again removed. Aliquots or the lower aqueous phase prior to and following the hexadecane freezing and thawing procedure were run on a 15% SDS-polycrylamide gel, as described in U. K. Lamemmli, Nature, 227, 1 (1971).

EXAMPLE 2—Extraction of Lysozyme from Human Saliva

Unstimulated, whole saliva was collected from one donor, and clarified by centrifugation at 12,000 g for 10 min. To 1 ml of clarified saliva was added 0.5 ml of hexadecane and the mixture vortexed for 2 min at room temperature. Following phase separation, the lower aqueous phase was removed. The hexadecane layer was washed with 1.0 ml PBS (phosphate buffered saline) including:

1. 8 g NaCl,
2. 0.2 g KCl,
3. 1.15 g Na$_2$HPO$_4$,
4. 0.2 g KH$_2$PO$_4$ and,
5. distilled water to one liter, pH 7.2.

The wash saline was subsequently removed and replaced with 1.0 fresh PBS.

Contents of the test tube were incubated at 4 C. so to solidify the hexadecane layer; the test tube was then allowed to equilibrate with room temperature, with concomitant melting of the hexadecane.

The foregoing is summarized in the following Table 1:

TABLE 1

| Sample | Relative Activity |
|---|---|
| Untreated clarified saliva | 1.00 |
| Following mixing with hexadecane | 0.30 |
| Activity adsorbed to interface following mixing procedure | 0.70 |
| Aqueous sample following solidification and | 0.30 |

TABLE 1-continued

| Sample | Relative Activity |
|---|---|
| melting of hexadecane layer | |

In order to assay lysozyme activity, 25 μl aliquots were applied in quadruplicate to paper pads (Schleicher and Schull, Dassel, West Germany, No. 321260). Following drying, the pads were placed on lawns of Micrococcus lysodeikticus (ATCC 4698) spread on nutrient agar plates. Following 18 h incubation at 30 C. the diameters of the inhibition zones were compared with those obtained using known salivary dilutions and the relative activity obtained by interpolation.

EXAMPLE 3—Extraction of Lysozyme from PBS

Lysozyme (Sigma, St. Louis, MO, No. L6876, from chicken egg white) was dissolved in 1 ml PBS to a final concentration of 200 g/ml and used fresh. To one ml of solution was added 0.5 ml hexadecane, and the mixture vortexed three times for two minute durations.

The lower phase was immediately removed and 1 ml of distilled water was added to the hexadecane. Desorption was carried out as described above. Twenty-five μl aliquots of the liquid removed prior to and following the solidification and melting procedure were assayed for enzyme activity as described in Example 1. Relative activity was calculated from two calibration curves obtained using various lysozyme concentrations, dissolved in water or PBS, respectively.

The foregoing is summarized in the following

TABLE 2

| Sample | Relative Activity |
|---|---|
| Solution prior to mixing with hexadecane | 1.00 |
| Solution following mixing with hexadecane Activity adsorbed to interface following mixing procedure | 0.56 |
| Aqueous sample following solidification and melting of hexadecane layer | 0.31 |

Following is a summary of the results illustrated by the foregoing examples:

When a commercial preparation of a mixture of seven marker proteins was vortexed in the presence of hexadecane in accordance with Example 1 above, one of the bands, corresponding to glyceraldehyde-3-phosphate dehydrogenase (G3PD), was almost completely removed from the aqueous phase, as observed by SDS-polyacrylamide electrophoresis of the mixture (FIG. 1, lane a). When the bottom aqueous phase was removed and replaced, and the hexadecane layer subsequently frozen and thawed, the enzyme was clearly eluted (FIG. 1, lane b).

Figure 2:
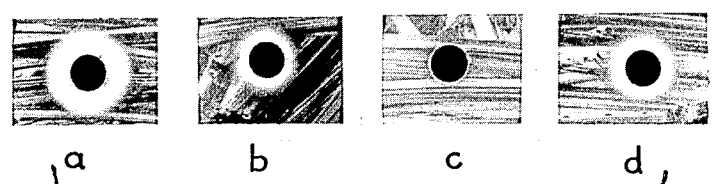
FIG. 2 illustrates the results produced in the adsorption and desorption of lysozyme from clarified human saliva, the lysozyme activity having been assayed on lawns of *Micrococcus lysodeikticus*.

FIG. 2 (lanes a–d) illustrate the absorption and desorption of lysozyme from clarified human saliva assayed on lawns of Micrococcus lysodeikticus as described above: (a) zone of inhibition of clarified human saliva; (b) loss of activity following mixing with hexadecane; (c) no significant activity observed in PBS wash of hexadecane layer; (d) reappearance of activity in aqueous phase following solidification and melting of hexadecane layer.

The mixing of whole, clarified saliva in the presence of hexadecane in accordance with Example 2 above brought about a 70% loss in lysozyme activity, as compared with that prior to mixing (Table 1 and FIG. 2). Forty-two percent of the activity lost in the mixing procedure (i.e., 30% of the original activity of the sample) could be recovered from the oil: water interface following phase transition of the hydrocarbon.

As shown in Example 3 and Table 2, lysozyme may be similarly extracted and eluted from PBS. In Table 2, lysozyme activity was measured by applying 25 l aliquots to paper pads, and measuring their zones of inhibition on lawns of Micrococcus lysodeikticus as described above. The Relative Activity was calculated from calibration curve using various salivary dilutions as described above. The loss in activity following mixing was presumably due to adsorption. Seventy percent of the activity removed from the PBS upon vortexing could be recovered from the distilled water following the freezing and thawing procedure. Elution into PBS, however, was less effective.

While the hexadecane is used as the liquid oil, it will be appreciated that other oils could be used, e.g., coconut oil, octadecane, preferably having melting points of −20° C. to 50° C. Coconut oil has a melting point of 21°–25° C., and when used, the extraction should preferably be at about 30° C.

The foregoing results indicate that certain proteins from commercial and biological mixtures can be removed to the aqueous: oil interface following a simple mixing procedure. Moreover, the desorbed proteins can be eluted by solidifying and melting the oil phase, concomitant with droplet coalescence. The finding that up to 70% of the lysozyme activity adsorbed to the aqueous:hexadecane interface could be recovered using this procedure indicates its potential for enzyme separation and purification, such as insulin, α-interferon, γ-interferon, antibody growth hormones.

The above method has several advantages which suggest its potential use in commercial purification techniques: (i) the commercial availability and low cost of hexadecane and other suitable liquid oils; (ii) the large potential interface available for adsorption on the oil droplets as compared with solid supports, and (iii) eluent addition is not required. It is clear that for specific separation purposes, various aspects of the procedure may be optimized, e.g., mixing energy and duration, composition of the aqueous and hydrocarbon phases.

While the invention has been described with respect to several preferred embodiments, it will be appreciated that many other variations, modifications and applications of the invention may be made.

What is claimed is:

1. The method for the separation or purification of biopolymers comprising the steps:
   adsorbing the biopolymer on the surface of liquid oil droplets;
   and separating the adsorbed biopolymer from the oil droplets.

2. The method according to claim 1, wherein the adsorbed biopolymer is separated from the oil droplets by mixing the droplets in an aqueous liquid, removing the aqueous phase and adding a fresh aqueous phase to the droplets, cooling the mixture to solidify and coalesce the oil and to cause it to release the adsorbed biopolymer to the fresh liquid, separating the fresh liquid and the biopolymer from the coalesced oil, and separating the biopolymer from the fresh liquid.

3. The method according to claim 1, wherein said oil droplets are of a liquid hydrocarbon having a melting point between −20° C. to 50° C.

4. The method according to claim 3, wherein said oil droplets are of hexadecane.

5. The method according to claim 1, wherein said adsorption is effected by mixing an aqueous solution containing the biopolymer with the liquid oil.

6. The method according to claim 5, wherein the aqueous solution is mixed with the liquid oil at room temperature.

7. The method for the separation or purification of biopolymers comprising the steps: adsorbing the biopolymer on the surface of liquid oil droplets; and separating the adsorbed biopolymer from the oil droplets by mixing the droplets in an aqueous liquid, removing the lower aqueous phase and adding a fresh aqueous phase to the droplets, cooling the mixture to solidify and coalesce the oil and to cause it to release the adsorbed biopolymer to the fresh liquid, separating the fresh liquid and the biopolymer from the coalesced oil, and separating the biopolymer from the fresh liquid.

8. The method according to claim 7, wherein said oil droplets are of a liquid hydrocarbon having a melting point between $-20°$ C. to $50°$ C.

9. The method according to claim 8, wherein said oil droplets are of hexadecane.

10. The method according to claim 8, wherein said adsorption is effected by mixing an aqueous solution containing the biopolymer with the liquid oil.

11. The method according to claim 10, wherein the aqueous solution is mixed with the liquid oil at room temperature.

12. The method for the separation or purification of biopolymers comprising the steps: adsorbing the biopolymer on the surface of liquid oil droplets by mixing an aqueous solution containing the biopolymer with the liquid oil; and separating the adsorbed biopolymer from the oil droplets.

13. The method according to claim 12, wherein the adsorbed biopolymer is separated from the oil droplets by mixing the droplets in an aqueous liquid, removing the lower aqueous phase and adding a fresh aqueous phase to the droplets, cooling the mixture to solidify and coalesce the oil and to cause it to release the adsorbed biopolymer to the fresh liquid, separating the fresh liquid and the biopolymer from the coalesced oil, and separating the biopolymer from the fresh liquid.

14. The method according to claim 12, wherein said oil droplets are of a liquid hydrocarbon having a melting point between $-20°$ C. to $50°$ C.

15. The method according to claim 14, wherein said oil droplets are of hexadecane.

16. The method according to claim 12, wherein the aqueous solution is mixed with the liquid oil at room temperature.

* * * * *